US005763407A

United States Patent [19]
Larsson et al.

[11] Patent Number: 5,763,407
[45] Date of Patent: *Jun. 9, 1998

[54] HIGH-PURITY DESMOPRESSIN PRODUCED IN LARGE SINGLE BATCHES

[75] Inventors: Krister Larsson; Thomas Mellbrand, both of Malmö ; Birgitta Mörnstam, Bunkeflostrand; Jan Roschester, Lund; Jan-Ake Sköldback, Malmö, all of Sweden

[73] Assignee: Ferring BV, Hoofddorp, Netherlands

[*] Notice: The portion of the term of this patent subsequent to Jun. 29, 2013, has been disclaimed.

[21] Appl. No.: 797,826

[22] Filed: Feb. 10, 1997

Related U.S. Application Data

[62] Division of Ser. No. 524,761, Sep. 7, 1995, Pat. No. 5,674, 850, which is a continuation of Ser. No. 176,411, Dec. 23, 1993, abandoned.

[51] Int. Cl.⁶ .......................... A61K 38/00; A61K 38/02; C07K 5/00; C07K 7/00
[52] U.S. Cl. .................................. 514/16; 514/15
[58] Field of Search ........................ 514/12, 13, 14, 514/15, 16, 17, 18; 530/328, 315

[56] References Cited

U.S. PATENT DOCUMENTS

| | | | |
|---|---|---|---|
| 3,497,491 | 2/1970 | Zaoral et al. | 260/112.5 |
| 3,794,633 | 2/1974 | Kamber et al. | 260/112.5 |
| 3,929,758 | 12/1975 | Hughes et al. | 260/112.5 |
| 4,033,940 | 7/1977 | Hughes et al. | 260/112.5 |
| 4,093,610 | 6/1978 | Abraham et al. | 260/112.5 |
| 4,216,141 | 8/1980 | Rivier et al. | 260/112.5 |
| 4,271,068 | 6/1981 | Kamber et al. | 260/112.5 |
| 4,351,764 | 9/1982 | Birr | 260/112.7 |
| 4,487,765 | 12/1984 | de Wied | 424/177 |
| 4,871,542 | 10/1989 | Vilhardt | 424/423 |
| 5,066,716 | 11/1991 | Robey et al. | 525/54.1 |
| 5,482,931 | 1/1996 | Harris et al. | 514/15 |
| 5,498,598 | 3/1996 | Harris | 514/11 |
| 5,500,413 | 3/1996 | Larsson et al. | 514/15 |
| 5,596,078 | 1/1997 | Andersson et al. | 530/315 |

*Primary Examiner*—Avis M. Davenport
*Attorney, Agent, or Firm*—Hopgood, Calimaede, Kalil & Judlowe, LLP

[57] ABSTRACT

A process for the manufacture of high purity desmopressin produced in single batches of substantial size and a method of treating diabetes insipidus with the high purity desmopressin produced therefrom.

3 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:1:

Tyr  Phe  Gln  Asn  Cys
        1                       5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:2:

```
Tyr  Phe  Gln  Asn  Cys  Pro
 1                 5
```

HIGH-PURITY DESMOPRESSIN PRODUCED IN LARGE SINGLE BATCHES

RELATED CASES

This is a divisional of application Ser. No. 524,761, filed Sep. 7, 1995, now U.S. Pat. No. 5,674,850 which is a continuation of Ser. No. 176,411, filed Dec. 23, 1993, now abandoned.

FIELD OF THE INVENTION

The present invention relates to high-purity desmopressin produced in single batches of substantial size and to a production method therefor. Furthermore, it relates to a method of treating diabetes insipidus by administration of single doses of desmopressin prepared from high-purity desmopressin that had been produced in single batches of substantial size, and to such single desmopressin doses.

BACKGROUND

The hormone analog 1-deamino-8-D-arginine vasopressin, (desmopressin, hereinafter also abbreviated "DDAVP"), is an important medicine for the treatment of diurea, such as associated with diabetes insipidus and nocturnal enuresis, and urine incontinence, and for the treatment of bleeding disorders such as hemophilia A, von Willebrand's disease and other conditions associated with platelet dysfunction.

Medium-size peptides can be routinely produced by a variety of multi-stop techniques in moderately pure form. Their impurity pattern and, thus, measures to be taken for their purification depend on the purity of reactants and reagents, the particular route of synthesis and reaction conditions in general. This further purification, however, often requires highly efficient purification methods, such as electrophoresis, or other methods which can only handle small amounts of peptide in a single run. Extensive purification also has a tendency to reduce yield, particularly when applied in the final synthetic steps.

These considerations also apply to the synthesis of DDAVP, which is usually isolated and medically used in form of its acetate.

While single batches of pure DDAVP thus may be obtained by use of conventional methods of synthesis and purification, the scale in which single batches of DDAVP can be prepared by these methods is unsatisfactory from an economic standpoint. In this specification, the term "single batch of DDAVP" signifies the DDAVP obtained in one single final step of DDAVP synthesis and purification. In view of the complexity of synthesis of DDAVP and other medium-size peptides, and also because of their often extremely high biologic activity, such single batch of substantial size is a batch containing product in the order of 500 g.

As rule, single DDAVP batches differ in, i.e., DDAVP-content and pattern of impurities. Documentation requirements for single batches, no matter whether small or large, include DDAVP-assay and tests such as specific optical rotation, absorbance, amino acid composition, content of related peptides, acetic acid and water. Since cost for analysis is substantial and identical for batches of all sizes, the production of DDAVP in single batches of substantial size, and DDAVP thus produced is desirable. There is, of course, also the usual benefit of economies of scale in producing high-purity DDAVP in single batches of substantial size.

OBJECTS OF THE PRESENT INVENTION

Accordingly, it is an object of the present invention to provide large single batches of high-purity DDAVP.

It is another object of the invention to provide an economical process by which large-size single batches of high-yield, high-purity DDAVP can be prepared.

It is a further object of the invention to provide a method of treating diabetes insipidus by administration of an adequate dose of DDAVP obtained from such single large batches, and such adequate dose.

SUMMARY OF THE INVENTION

In accordance with the present invention, there are provided single batches of desmopressin of at least 50 g, preferably at least 100 g, particularly preferred of at least about 500 g in weight, containing respectively no less than 44 g, preferably 88 g, particularly preferred about 440 g (95.0 % by weight) of $C_{46}H_{64}N_{14}O_{12}S_2$, and a process for producing the same. Also provided are single batches of desmopressin having a weight of at least about 50 g, preferably 100 g, particularly preferred about 500 g, containing no less than 98.5% by weight of desmopressin in respect of adjoining matter other than acetic acid and water, and a process for producing the same. The desmopressin batches according to the invention thus do not contain more than a total of 1.5% by weight of adjoining matter other than water and acetic acid, i.e. no more than 1.5% by weight of impurities. Acetic acid is chemically bound to the basic desmopressin, which is provided by the inventive process as an acetate of varying stoichiometry. Desmopressin batches according to the invention also contain small amounts of water which only can be removed with difficulty. Such adjoining acetic acid or water do not impair the pharmacological properties of desmoprossin. Such high-purity desmopressin batches, therefore, will usually contain a total of at least about 3.5% by weight of acetic acid and water.

The inventive process is characterized by comprising a final synthetic step, in which at least 100 g, preferably 200 g, particularly preferred at least about 500 g, of $R^1$-mercaptopropionyl-Tyr-Phe-Gln-Asn-Cys($R^2$)-Pro-D-Arg-Gly-NH$_2$, (SEQ ID NO:1) $R^1$ and $R^2$ being, independently of each other, selected from acetamidomethyl and triphenylmethyl, are dissolved in a protic solvent at neutral or slightly acidic conditions to form a reactant solution, a second solution of iodine in a protic solvent is introduced into said reactant solution under agitation, resulting in a reactant/reagent solution, the amount of iodine being at least about stoichiometric in respect of said $R^1$-mercaptopropionyl-Tyr-Phe-Gln-Asn-Cys($R^2$)-Pro-D-Arg-Gly-NH$_2$ (SEQ ID NO:1), a disulfide moiety-forming reaction is supported in said admixture until substantially complete formation of desmopressin, wherein said the temperature of said admixture is not allowed to exceed 50° C., thus forming a pre-purified solution of desmopressin; the pre-purified desmopressin solution is applied to a separation column containing cation exchange resin equilibrated with acid and desmopressin is eluted; the eluted, at least 98.5% pure (in respect of adjoining matter other than water and acetic acid) desmopressin is isolated in a single batch weighing at least 50 g, preferably at least 100 g, particularly preferred at least 500 g, containing, in addition to minor amounts of acetic acid and water, no less than, respectively, 44 g, 88 g, and 440 g of $C_{46}H_{64}N_{14}O_{12}S_2$ and no more than, respectively 660 mg, 1.32 g, and 6.6 g of impurities, i.e. adjoining matter other than water and acetic acid.

It is preferred for the derivative of 1-mercaptopropionyl-Tyr-Phe-Gln-Asn-Cys-Pro-D-Arg-Gly-NH$_2$ (SEQ ID NO:2) to be β-acetamidometylmercapto-propionyl-Tyr-Phe-Gln-Asn-Cys(S-acetamidomethyl)-Pro-D-Arg-Gly-NH$_2$ (SEQ ID NO:1).

It is also preferred to elute desmopressin with a buffered solution, particularly with a buffered solution comprising ammonium acetate/acetic acid.

If desired, the at least 95% pure desmopressin obtained by the process according to the invention may be further purified by conventional means, such as electrophoresis, gel permeation chromatography, chromatography, including reverse-phase chromatography, etc. Further purification by gel permeation chromatography and/or reverse phase chromatography is preferred.

At about ambient temperature the cation exchange resin should be substantially stable in contact with iodine dissolved in protic solvents. Preferred resins are based on cross-linked agarose substituted with methylsulfonyl groups, such as S-Sepharose® FF.

Furthermore, the invention discloses desmopressin with a purity of at least 98.5% in respect to other adjoining matter than acetic acid and water, i.e. with a content of impurities of less than 1.5%, produced in batches of at least 50 g, preferably of at least 100 g, particularly preferred of at least about 500 g, for use as a medicine, particularly a medicine for the treatment of various urinary disorders, such as diabetes insipidus, incontinence and enuresis, and dysfunctions of the coagulative system, such as hemophilia A, von Willebrand's disease, platelet dysfunction and other bleeding indications. Such batches of high-purity desmopressin may be used for the manufacture of a medicament intended for treatment of the aforementioned medical disorders.

Further features and advantages of the present invention are evident from the description of a preferred embodiment and the appended claims.

EXAMPLE 1

Boc-Gln-Asn-Cys(Acm)-Pro-OH (X)

BocCys(Acm)ONp is prepared from BocCys(Acm)OH (Novabiochem, Läufalingen, CH) and p-nitrophenol by reaction with N,N'-dicyclohexylcarbodiimide (DCC) in ethyl acetate and used without purification for the preparation of Boc-Cys(Acm)-Pro-OH (XII) by reacting it with H-Pro-OH in DMF/etyl acetate/HCl at 0° C. while keeping pH neutral by addition of $Et_3N$. Yield 81%. Purity>95% (TLC). Boc-Asn-Cys(Acm)-Pro-OH (XIII) is obtained by deblocking XII in HCl/HOAc at room temperature, dissolving the thus obtained raw H-Cys(Acm)-Pro-OH.HCl in DMF and neutralizing it with $Et_3N$, and adding Boc-Asn-ONp (Novabiochem, Läufelingen, CH) at −5° C. while keeping pH neutral. XIII is isolated in 81% yield. $[a]_D^{20}$=−77.1° (1 g/100 ml DMF). The tetrapeptide derivative X is prepared from XIII and Boc-Gln-ONp (Novabiochem, L aufelingen, CH) in a way corresponding to the preparation of XIII from XII and Boc-Asn-ONp. Yield 78.5%; $[a]_D^{20}$=−89.7° (1 g/100 ml $H_2O$).

EXAMPLE 2

Mpa(Acm)-Tyr-Phe-NHNH$_2$ (XI)

Mpa(Acm)-Tyr-OEt (XIV) is prepared by reacting H-Tyr-OEt.HCl with Mpa(Acm)-OH (Bachem AG, CH) and DCC in DMF containing 1-hydroxybenzotriazole (HOBt) at 0° while maintaining pH at 7 ($Et_3N$). Yield 48%. The hydrazide XI is prepared by reacting the ester XIV with H-Phe-$N_2H_3$ in DMF/$H_2O$ under catalysis by α-chymotrypsin. Yield 90%; m.p. 240°–242° C.

EXAMPLE 3

Mpa(Acm)-Tyr-Phe-Gln-Asn-Cys(Acm)-Pro-OH (SEQ ID NO:1) (VII)

Boc-Gln-Asn-Cys(Acs)-Pro-OH (X; 600 g) is dissolved in 56 ml trifluoroacetic acid (TFA) which is evaporated after being kept for one hour at room temperature. The residue is dissolved in 970 ml dimethyl formamide (DMF) and cooled, and pH is adjusted to 7 ($Et_3N$). Mpa(Acm)-Tyr-Phe-NHNH$_2$ (XI; 564 g) is dissolved in 5.9 l DMF, the solution is cooled to −18° C., HCl/ethyl acetate (810 ml; 3.2M) is added and the solution is kept at −15° C. Isoamylnitrite (180 ml) is added and the solution is stirred at about −10° C. for 15 min. After cooling to −20° C. pH is adjusted to 7 ($Et_3N$) The solution of the deblocked tetrapeptide in DMF is added and the mixture stirred at −5° C. After the reaction is virtually complete (99.5% conversion of the deblocked tetrapeptide as determined by TLC), precipitated salt is filtered off and the volume reduced to 3.1 ml by evaporation in vacuo. EtOH (99.5%; 215 ml) is added and the solution heated to 60° C. After cooling to ambient temperature pH is adjusted to 2.5 (conc. HCl). The precipitate is filtered off, washed with 99.5% EtOH, and dried to yield 903 g of white crystals; yield 85%, mp. 188°–191° C.

EXAMPLE 4

Boc-D-Arg(HCl)-Gly-NH$_2$ (VIII)

H-Gly-NH$_2$.HCl (168 g) and 1-hydroxy-benzotriazole (HObt; 213 g) is suspended in 34 ml DMF and the solution is cooled to −10° C. $Et_3N$ (129 ml) is added and the mixture stirred for 15 min. Boc-D-arginine(HCl) (439 g) is added and the temperature brought to 0° C. DCC (290 g) dissolved in 4.5 ml DMF is added and pH adjusted to 6.0 ($Et_3N$). After complete conversion, the formed precipitate is removed by filtration and the filtrate evaporated in vacuo. The residue is dissolved in 5.2 l water, the solution is cooled to 0° C. and pH adjusted to 3 (1M HCl). After removing HOBt by filtration the solution is extracted with dichloromethane. The aqueous phase is reduced to a volume of 1.3 l in vacuo, subjected to azeotropic distillation with butanol (4×), and its volume brought to 4.4 l by addition of butanol. The solution is extracted with 0.1M HCl containing 10% NaCl (w/w) and 5% butanol (v/v), and thereafter reduced to half its volume by distillation. After repeating the azeotropic distillation with butanol and removing NaCl by filtration, the solution is poured into an eightfold excess (v/v) of isopropyl acetate, and the precipitate is collected by filtration and washed with isopropyl acetate. Compound VIII was obtained in form of a white amorphous powder; yield 439 g (90%), $[a]_D^{20}$=+4.3° (1 g/100 ml DMF).

EXAMPLE 5

Mpa(Acs)-Tyr-Phe-Gln-Asn-Cys(Acm)-Pro-D-Arg(HCl)-Gly-NH$_2$ (SEQ ID NO:1) (IX).

BOC-D-Arg(HCl)-Gly-NH$_2$ (VIII; 439 g) is dissolved in 1.5 l acetic acid and 1.3 l HCl/HOAc (2.2M) is added.

After stirring for 1.5 h at room temperature, the solution is evaporated under reduced pressure and the residue dissolved in 1.9 l DMF. The deblocked dipeptide is precipitated in form of oily droplets by adding xylene (2 l). After decantation of the supernatant, the residue is washed with xylane and remaining solvent removed in vacuo. The residue is dissolved in 7.1 l DMF and the solution cooled to −10° C. By addition of $Et_3$ pH is adjusted to 7.5.

Mpa(Acm)-Tyr-Phe-Gln-Asn-Cys(Acm)-Pro-OH (SEQ ID NO:1) (VII; 903 g) and 129 g HOBt are dissolved in 4.2 l DMF and the deblocked dipeptide H-D-Arg(HCl)-Gly-NH$_2$ in DMF obtained in the preceding stop and the calculated amount of DCC is added. After 90% conversion (TLC)

DCU is filtered off and and the solution reduced to a volume of 6.5 l, heated to 60° C. and poured into 20 l EtOH/EtOAc 85:15 (v/v). The precipitate is collected by filtration and washed with EtOH/EtOAc 85:15. Compound IX was obtained in form of a white powder (yield 1 kg (84.9%), m.p. 182°–185° C.) with a purity of 94.5% (HPLC).

EXAMPLE 6

Mpa—Tyr—Phe—Gln—Asn—Cys—Pro—D—Arg—Gly—NH$_2$ (SEQ ID NO: 2) (desmopressin)
|_____|

IX (1 kg) is dissolved in 1,000 l acetic acid/water 1:9 (v/v). The blocked nonapeptide derivative IX is oxidized at room temperature by addition of 200 g iodine dissolved in 8 l ethanol by means of a roller pump, the feeding speed of which is being controlled by a UV-monitor in order to keep the amount of free iodine in the reaction medium low. Conversion of IX is monitored by HPLC. A yellow colour persists after the entire amount of IX has been consumed. The solution from the reaction containing the products is passed through a short stainless steel column containing 160 l S-Sepharose® FF (Pharmacia, Sweden) equilibrated with aqueous acatic acid. The title compound is eluted with 0.08M NH$_4$Ac/AcOH buffer (24 l, pH 4.1; fractions monitored by HPLC analysis). Fractions containing compound I in purity>98.5% (disregarding from buffer components) are combined. The solution containing the acetate of pure title compound is concentrated by partial evaporation of solvent in vacuo or by reverse osmosis, and finally freeze dried to obtain a white fluffy powder.

Compound (I) is further purified by gel filtration on Sephadex G25 (0.1M acetic acid). Elution is followed by analyzing individual fractions with HPLC. The combined fractions containing pure product are combined and freeze dried. Desmopressin (in form of the acetate) is obtained in a purity of>98.5% as a white fluffy powder. Yield 440 g.

Peptide-related desmopressin impurities and desmopressin content are determined by HPLC (principle of method: Ph Eur. 2nd Ed., p.V.6.20.4). Impurities: Lichrospher RP-18, 5µ (4-4) mm column; loop vol. 20 µl; flow rate 1.5 ml/min; UV-detector at 220 nm; isocratical elution; mobile phase acatonitrile/0.067M phosphate buffer (pH 7.0) 17:83 (v/v). Measurement of peak area; calibration by external standard. Content: same conditions, except for elution by aetonitrile/phosphate buffer gradient varying from 12:88 to 26:74 (v/v)

The experimental procedure describing the production of a batch of about 440 g of high-purity desmopressin has been downscaled by such adaptation of volumes and weights as being in within the easy reach of a person skilled in the art to produce about 44 g of desmopressin to essentially the same standards of purity.

---

What is claimed is:

1. A method for treating diabetes insipidus, hemophilia A and von Willebrand's disease, comprising oral, nasal or intravenous administration of a dose of desmopressin effective to produce a physiological effect, said desmopressin produced in a single batch having a weight of at least about 50 g containing at least 98.5% by weight of desmopressin ($C_{46}H_{64}N_{14}O_{12}S_2$) in respect of adjoining matter other than water and acetic acid, said batch produced with a final synthetic step in which at least about 1 kg of mercapto-propionyl-Tyr-Phe-Gln-Asn-Cys-Pro-D-Arg-Gly-$NH_2$ (SEQ ID NO: 2) or a derivative thereof, said derivative being stable at neutral or slightly acidic conditions, is dissolved in a protic solvent at neutral or slightly acidic conditions to form a reactant solution into which a second solution of iodine in a protic solvent or solvent mixture is introduced under agitation to form a reactant/reagent solution in which desmopressin is being formed.

2. A single oral dose of desmopressin effective to produce a physiological effect for treatment of diabetes insipidus, hemophilia A and von Willebrand's disease, said dose prepared from a desmopressin batch produced in single batches of desmopressin having a weight of at least about 500 g containing at least 98.5% by weight of desmopressin ($C_{46}H_{64}N_{14}O_{12}S_2$) in respect of adjoining matter other than water and acetic acid, said batches produced with a final synthetic step, in which at least about 1 kg of mercapto-propionyl-Tyr-Phe-Gln-Asn-Cys-Pro-D-Arg-Gly-$NH_2$ (SEQ ID NO: 2) or a derivative thereof, said derivative being stable at neutral or slightly acidic conditions, is dissolved in a protic solvent at neutral or slightly acidic conditions to form a reactant solution into which a second solution of iodine in a protic solvent or solvent mixture is introduced under agitation to form a reactant/reagent solution in which desmopressin is being formed.

3. A single oral dose of desmopressin effective to produce a physiological effect for treatment of diabetes insipidus, hemophilia A and von Willebrand's disease, said dose prepared from a single batch of desmopressin containing no less than 44 g of desmopressin ($C_{46}(H_{64}N_{14}O_{12}S_2$) and no more than a total of 1.5% by weight of adjoining matter with respect to desmopressin ($C_{46}H_{64}N_{14}O_{12}S_2$) other than water and acetic acid.

* * * * *